United States Patent [19]
Shippert

[11] Patent Number: 6,123,697
[45] Date of Patent: *Sep. 26, 2000

[54] PRESSURE APPLYING FLUID TRANSFER METHOD

[76] Inventor: Ronald D. Shippert, 4975 S. Albion St., Littleton, Colo. 80121

[ * ] Notice: This patent is subject to a terminal disclaimer.

[21] Appl. No.: 09/169,741

[22] Filed: Oct. 8, 1998

Related U.S. Application Data

[63] Continuation of application No. 08/649,997, May 16, 1996, Pat. No. 5,827,224, which is a continuation-in-part of application No. 08/561,869, Nov. 22, 1995, Pat. No. 5,713,855.

[51] Int. Cl.[7] ................................................. A61M 31/00
[52] U.S. Cl. .................... 604/514; 604/104; 604/540; 606/196
[58] Field of Search .................... 606/191–192, 606/196; 604/1–2, 11, 19, 500, 514, 104, 174–175, 284, 512, 540

[56] References Cited

U.S. PATENT DOCUMENTS

| | | | |
|---|---|---|---|
| 1,355,846 | 10/1920 | Rannells . | |
| 3,049,125 | 8/1962 | Kriwkowitsch | 128/325 |
| 3,570,494 | 3/1971 | Gottschalk | 128/325 |
| 4,030,504 | 6/1977 | Doyle | 128/325 |
| 4,883,465 | 11/1989 | Brennan | 604/96 |
| 4,950,280 | 8/1990 | Brennan | 606/196 |
| 5,011,474 | 4/1991 | Brennan | 604/54 |
| 5,308,338 | 5/1994 | Helfrich | 604/175 |
| 5,324,518 | 6/1994 | Orth et al. | 424/423 |
| 5,336,163 | 8/1994 | Demane et al. | 602/46 |
| 5,358,494 | 10/1994 | Svedman | 604/313 |
| 5,370,656 | 12/1994 | Shevel | 606/196 |
| 5,374,261 | 12/1994 | Yoon | 604/385 |
| 5,713,855 | 2/1998 | Shippert . | |
| 5,827,224 | 10/1998 | Shippert . | |

*Primary Examiner*—Mark Bockelman
*Attorney, Agent, or Firm*—Sheridan Ross P.C.

[57] ABSTRACT

A device for applying pressure using absorbed fluid is disclosed. The device has particular utility in body cavities, such as nasal or sinus passages. In one embodiment, the device includes an expandable packing member and a delivery/draining tube. The packing member is insertable into a body cavity or body wound and expands when the packing member absorbs one or more fluids. After reaching the desired expansion, the packing member contacts body walls and applies pressure thereto. The delivery/draining tube is able to deliver fluid for treatment purposes or for expanding the packing member to a desired size. The delivery/draining tube is also used in removing body or other fluids from the body cavity or wound that are absorbed by the packing member. Rehydrating fluid is also utilized in facilitating the removal of the packing member from the body cavity or wound. In another embodiment, the packing member is definable to include anterior, body and posterior sections. A wrap member is disposed about portions of the anterior section that inhibits expansion thereof by liquid, as well as preventing adhesion or unwanted engagement between said anterior section portions and parts of the body cavity in which the packing member is inserted.

13 Claims, 12 Drawing Sheets

PRESSURE APPLYING FLUID TRANSFER METHOD

This is a continuation application of pending prior application Ser. No. 08/649,997 filed May 16, 1996 U.S. Pat. No. 5,827,224 which is a continuation-in-part of application Ser. No. 08/561,869 filed Nov. 22, 1995 U.S. Pat. No. 5,713,855.

FIELD OF THE INVENTION

The present invention relates to a body opening packing device for absorbing body fluid and, in particular, to a device that absorbs blood and applies pressure to body opening walls while being able to deliver and remove fluids from the body opening.

BACKGROUND OF THE INVENTION

After certain surgical procedures or because of bodily injuries, it is often times necessary to utilize a packing device. The packing device is made of a material that is able to absorb blood or other body fluids. The packing device is typically inserted into the body cavity that requires packing and absorbing of blood or other body fluids. The packing device absorbs the blood and must, on many occasions, be removed for replacement with a new packing device. Such insertions and removals of packing devices can be a traumatic experience for the patient, or at least constitute an unwanted degree of discomfort. Furthermore, even though the packing device might include a pad that absorbs the blood and which is intended to be shaped in order to conform to the particular body cavity into which it is inserted, such an absorbing pad may still not be desirably configured to best contact the body cavity walls for absorbing the blood and for applying pressure where it needs to be applied in order to control the bleeding.

With respect to the control of bleeding in body cavities, such as nasal passages, it is known in the prior art to utilize an inflatable member, such as a balloon, which applies pressure to the wall or walls of the body cavity. Such devices are intended to attempt to avoid patient discomfort or trauma while still effectively controlling the bleeding. However, such devices are deficient in absorbing body fluids or being able to deliver desired fluids, such as a saline solution, to the body cavity. Medical devices that deliver desired fluids to the body, for example after a particular surgical procedure, do not also apply pressure to the walls of the body cavity. Such devices are commonly used to prevent infections from occurring or treat wounds that have become infected. Such devices are not intended for generally open body cavities that require pressure in order to control bleeding.

Numerous and different medical devices have been advanced or devised for use in the treatment or care of patients in order to control bleeding. Certain known medical devices are involved with the treating of wounds or other body parts due to a surgical procedure that was performed. Such treatment includes the irrigating and/or draining of the body cavity or wound. However, it would be advantageous to provide a medical device that combines a number of functions in one unit while minimizing or reducing the discomfort or traumatic impact on the patient because of the usage of such a medical device.

SUMMARY OF THE INVENTION

In accordance with the present invention, a medical device is provided that applies pressure to one or more body walls to control flow of body fluids, while being able to drain or remove such fluids. This medical device is also useful in delivering an irrigating or treating fluid to the body opening. In certain embodiments, the medical device is utilized in applying pressure in a nasal passage or a sinus passage, while at selected times providing a desired fluid to or draining body fluids from the nasal passage.

The medical device includes an expandable packing member or pad that is generally elongated. The packing member has rounded or curved corners to facilitate insertion of the packing member into the body cavity, while reducing possible discomfort to the patient. The packing member is preferably made of a polyvinyl alcohol (PVA) foam that is expandable to about 1.5–7 times its unexpanded size. The packing member preferably has the same thickness throughout a substantial majority of its length when the packing member is unexpanded.

The packing member includes a channel formed through at least portions of the longitudinal extent thereof. The channel is generally cylindrical in shape for receiving a section or portions of a delivery/draining tube. In one embodiment, the channel extends substantially throughout the longitudinal extent of the packing member. The delivery/draining tube includes at least one hole and preferably a number of holes formed therein along the section thereof that is positioned in the channel. Once located in the channel, this section of the delivery/draining tube is fixedly held in place and unable to slide relative to the delivery/draining tube. In an embodiment in which there are a number of holes, they are located throughout the circumference of the delivery/draining tube.

A fluid transfer unit is connected to the delivery/draining tube at the opposite end from that section held in the channel of the packing member. In one embodiment, the fluid transfer unit is a conventional syringe having a luer that mates with the delivery/draining tube end. The fluid transfer unit is able to contain an irrigating fluid, such as a saline solution, that is deliverable through the hole or holes in the delivery/draining tube for passage through the packing member into the body cavity or the body cavity walls. Alternatively, the fluid transfer unit is able to draw or remove fluid that is absorbed by the packing member and received from the packing member into the delivery/draining tube through the holes thereof.

In another embodiment, the medical device further includes a venting tube that is disposed in the channel with the delivery/draining tube. The venting tube enables the patient to breathe through the nose when the medical device is used in a nasal passage. The venting tube can be defined as having a distal end and a proximal end. The distal end of the venting tube extends through the packing member. The proximal end terminates at the opposite end of the packing member. In one embodiment, this termination is at an angle different from 90 degrees to advantageously facilitate breathing using the venting tube.

In operation, the packing member is inserted into a body opening, such as a body cavity or body wound, that has one or more body walls. In the case of a nasal pack, for example, the packing member is useful in controlling bleeding and providing a desired irrigating fluid. Once in position, the packing member is able to absorb the blood or other body fluid. Upon sufficient fluid being absorbed, the fluid migrates through the holes in the delivery/draining tube where it can be drawn away by the fluid transfer unit. Alternatively, a fluid can be supplied from the fluid transfer unit to the delivery/draining tube where the fluid is received by the packing member and expands the packing member. As a further but related alternative, both body fluid and delivered fluid are used in causing the packing member to expand due to the absorption by the packing member of both of these fluids. Upon expanding to another size, the packing member applies pressure to one or more body walls in the body cavity. Over time or at additional times, irrigating fluid can be delivered from the fluid transfer unit through the packing member for treating the particular body part into which the packing member is inserted. An important aspect of the operation of the present invention involves the providing of a rehydrating fluid substantially immediately before the packing member is removed from the body cavity. The packing member over time may dry out or lose sufficient fluid so that, when withdrawn or removed from the body cavity, such removal can cause discomfort or result in trauma to the patient. This is avoided by causing the packing member to absorb sufficient fluid for removal while not delivering so much fluid that removal of the packing member cannot be accomplished without discomfort. With respect to applying the desired or needed pressure to a body wall, as part of the procedure in using the medical device, the physician or other user may determine by observation that the amount of expansion due to absorption of body fluid is insufficient to achieve such a pressure. Consequently, further fluid is provided to the packing member from the fluid transfer unit.

In another embodiment, a medical device is provided that includes, as part of an integral packing member, different geometrically configured sections to better absorb body fluid and apply desired pressure to the nasal cavity. This packing member includes a posterior section, an anterior section and a body section between the posterior and anterior sections. Preferably, an anchor member is joined to the anterior section and acts to prevent unwanted movement of the packing member inwardly relative to the nasal cavity so that the packing member does not move in a direction inwardly of a body air passageway. A wrap member is disposed about portions of the anterior section to prevent it from unwantedly adhering to nasal cavity walls. Such portions, in the absence of the wrap member, would be exposed to the air and could readily adhere to tissue or other parts of the nasal cavity. If such occurs, tissue healing, such as a scab, could be jeopardized by removal of the packing member. This embodiment of a medical device may also include a delivery (irrigating)/draining tube. With respect to the geometric configuration of the packing member, the body or mid section has a greater height than each of the posterior and anterior sections. The posterior section has a greater width than the anterior and body sections to provide desired fitting or anchoring at the posterior end of the packing member.

Based on the foregoing summary, a number of salient features of the present invention are readily discerned. A medical device is disclosed that includes a packing member for placement relative to a body cavity or body wound. The packing member expands due to absorption of body fluid and/or a fluid received from a fluid transfer unit, such as an irrigating fluid, an antibiotic, an anesthetic or decongestant. When insufficient body fluid is available to be absorbed by the packing member and apply the desired necessary pressure, fluid can be delivered to the packing member to cause further expansion, which results in the desired or needed pressure being applied. The body fluid, such as blood, can be withdrawn through a delivery/draining tube into the fluid transfer unit. Consequently, the number of times that a packing member needs to be replaced due to absorption of too much fluid is substantially reduced. The fluid delivery aspect of the present invention enables desired treating or healing-assisting fluids to be delivered to the body cavity without removal of the packing member, which facilitates this procedure and reduces the possibility of traumatizing the patient. With respect to removal of the packing member, the present invention eliminates potential discomfort or trauma to the patient due to a dried out packing member since fluid can be delivered to the packing member immediately before its removal so that the packing member is sufficiently pliable and soft. In another embodiment, a wrap member, made from a different, impermeable material, is disposed about an anterior section of the packing member. This prevents unwanted contact and adhesion between this portion of the packing member and the nasal cavity wall in order to facilitate removal of the packing member.

Additional advantages of the present invention will become readily apparent from the following discussion, particularly when taken together with the accompanying drawings.

DETAILED DESCRIPTION

Figure 1:
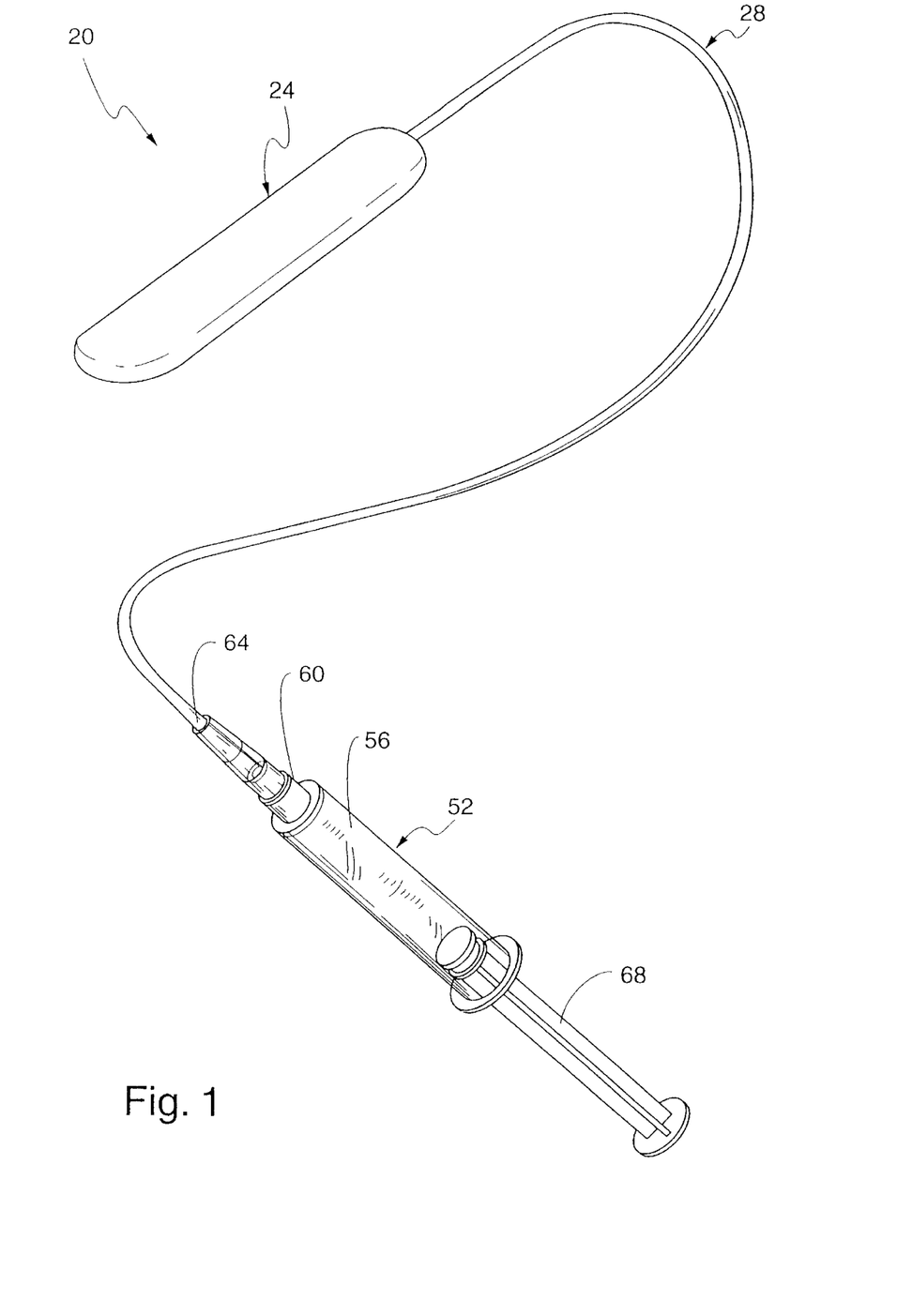
FIG. 1 illustrates the medical device of the present invention for absorbing body fluids, applying pressure to body walls in a body cavity and providing fluid to the body cavity.

With reference to FIG. 1, a device 20 based on the present invention is illustrated. The device 20 includes a packing member or foam pad 24 that is generally elongated in shape. At the ends along its length, the packing member has rounded or curved corners to facilitate placement of the packing member 24 in a body cavity. The packing member 24 is made of a material that absorbs fluids, including body fluids, such as blood. In certain embodiments, the packing member 24 is made from a polyvinyl alcohol (PVA) or polyurethane foam or sponge, or other foam materials, which is formed or manufactured into desired sizes for placement in a particular body cavity. As illustrated in FIG. 1, the packing member 24 is initially in a compressed or unexpanded state. When the packing member 24 absorbs fluids, it is able to expand to a desired size. In one embodiment, the thickness along most of the length of the packing member 24, when placed in a body cavity, expands upon receiving fluid to about 1.5–7 times its compressed or unexpanded state. As can be understood, the portions of the packing member that expand are dependent upon their location in the body cavity. Little or no expansion occurs of those portions of the packing member 24 that contact a wall of the body cavity.

Figure 2:
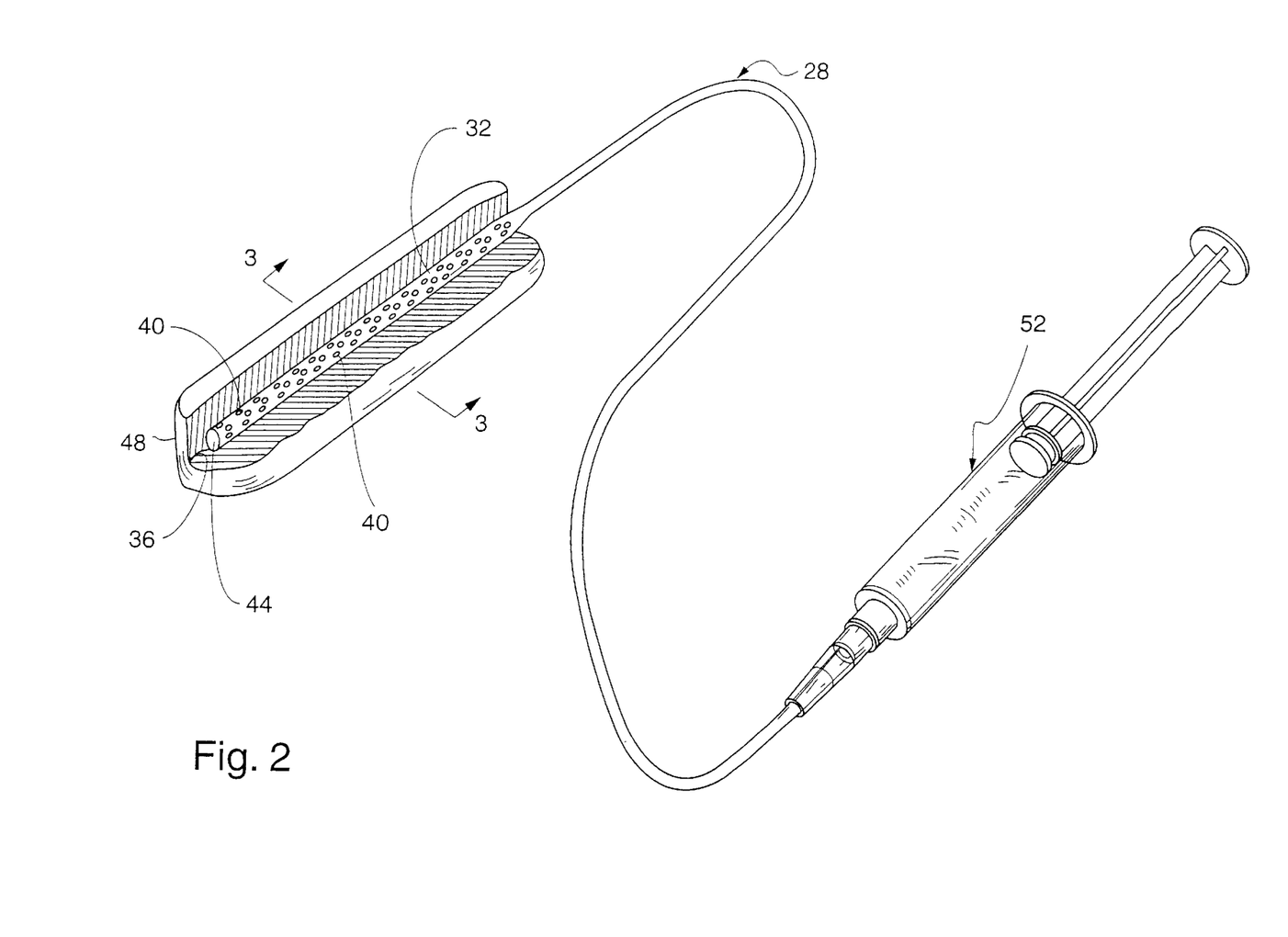
FIG. 2 is a cut-away view of the packing member that illustrates the delivery/draining tube section within the body of the packing member.
Figure 3:
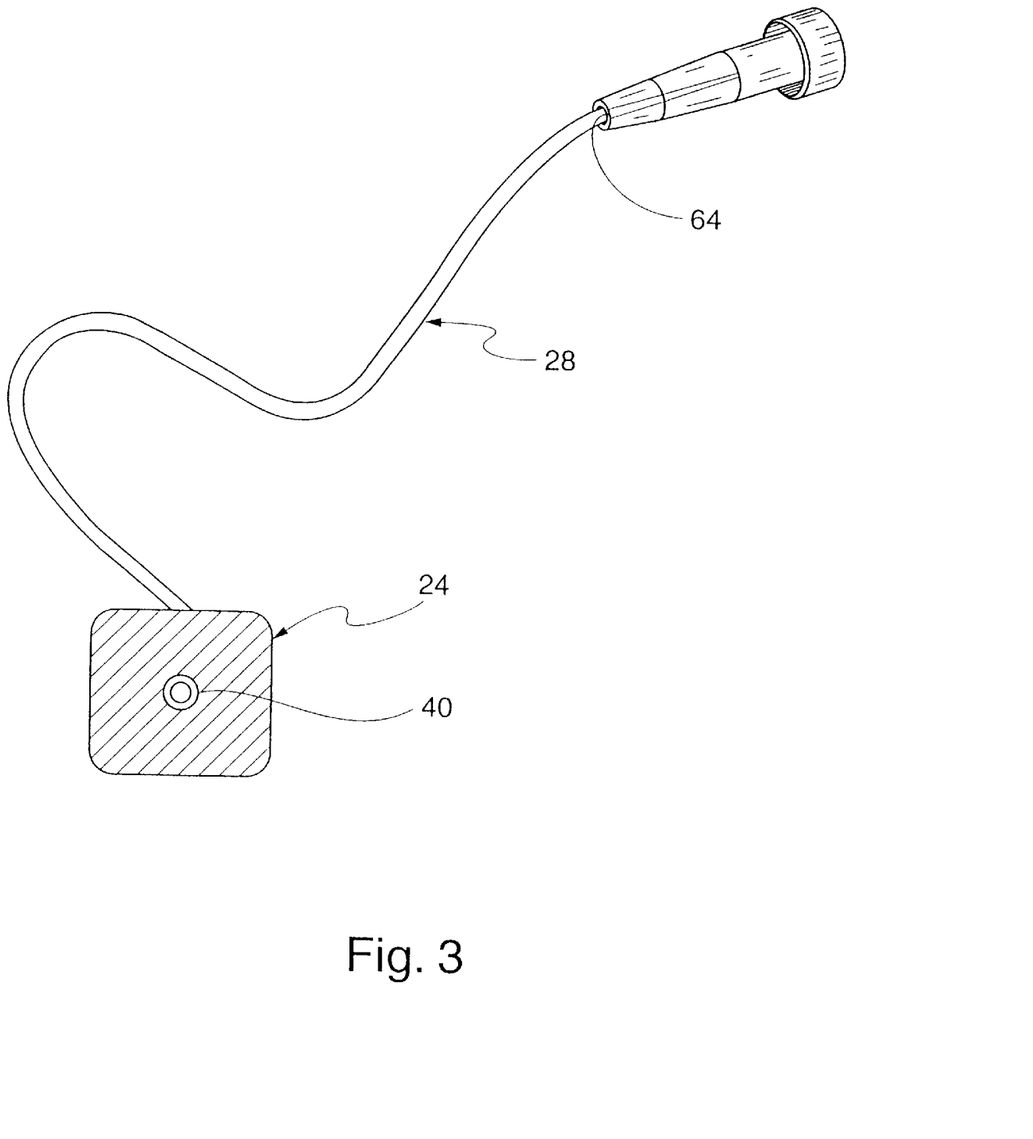
FIG. 3 illustrates a lateral cross-section of the packing member showing the delivery/draining tube disposed within the body of the packing member.

The medical device 20 also includes a delivery/draining tube 28, which is able to carry fluids both to and from the packing member 24. As seen in FIG. 2, the delivery/draining tube 28 has a channel section 32 that is disposed in a channel 36 provided or formed in the body of the packing member 24.

The channel section 32 is fixedly held in the channel 36, i.e., it does not slide nor is there any intended relative movement between the packing member 24 and the channel section 32. In one embodiment, the fixed attachment is accomplished, at least in part, by providing the width or diameter of the channel 36 so that it is less than the outside diameter of the channel section 32. Preferably, the channel section 32 has the same diameter and is integral with the remaining portions of the delivery/draining tube 28. In order for the delivery/draining tube 28 to transfer fluid relative to the packing member 24, it includes at least one hole through which fluids are able to pass. In the embodiment of FIG. 2, a plurality of holes 40 are illustrated. The holes 40 are provided throughout the length of the channel section 32 and are also provided along the entire outer periphery or circumference of the channel section 32. The fluid transfer relative to the holes 40 can be bi-directional. More specifically, excess body fluid, such as blood, that is present in the body cavity having the packing member 24, is absorbed by the packing member 24 and passes inwardly of its body to the channel 36 where such fluid passes through the holes 40. Such fluid can be carried or drawn along the delivery/draining tube 28 away from the packing member 24. Alternatively, the holes 40 are able to pass a delivery fluid that is carried to the packing member 24. The channel section 32 has a plugged end 44 that terminates the delivery/draining tube 28. The plugged end 44 is formed by creating a knot in the channel section and while this end is outside of the distal end 48 of the packing member. After the knot is formed, the knot is pulled back into or at the distal end 48.

In other embodiments, the length of the channel section 32 and/or the number of holes 40 can differ. By way of example only, the channel section 32 of the delivery/draining tube 28 might be less than the length of the packing member 24, such as even less than one half the length of the packing member 24. In another embodiment, the length of the channel section 32 may essentially be the same length as illustrated in FIG. 2; however, the spacing between holes may be greater and/or the number of holes may be more or less than that illustrated in FIG. 2. In yet another embodiment, the number of holes 40 at one portion of the channel section 32 may be greater than at other portions thereof whereby greater fluid transfer occurs at such portions.

With regard to dimensions related to the packing member 24 and channel section 32 including the holes 40 thereof, the diameter of the delivery/draining tube channel section 32 is at least 5 percent of the thickness of the packing member in its compressed or unexpanded state and the diameter of the delivery/draining channel section 32 is no greater than about 80 percent of the thickness of the packing member 24 in its compressed or unexpanded state. In the preferred embodiment, the amount of the packing member 24 that surrounds the channel section 32 of the delivery/draining tube 28 is about 1–9 millimeters. The packing member 24, especially in an application as a nasal pack, has substantially the same thickness throughout a substantial majority, at least 75 percent, of its length when the packing member is in its compressed state. Regarding the length of the delivery/draining tube, when the medical device 20 is used in connection with a nasal application, it is preferred that the length be sufficient to enable portions of the delivery/draining tube 28 to be placed over the ear of the patient and attached to the head of the patient. In many applications, the length of the delivery/draining tube 28 is at least twice the length of the packing member 24.

The medical device 20 also includes a fluid transfer unit 52 that is able to deliver and remove fluids using the delivery/draining tube 28. More specifically, the fluid transfer unit 52 is able to operate in one of two selected modes, namely: transferring fluids to the packing member 24 or transferring fluids from the packing member 24. In delivering fluids to the packing member 24 and thereby to the body cavity in which the packing member 24 is located, the fluid transfer unit 52 has a fluid with desired characteristics or properties that is to be delivered to the body cavity, such as a saline solution, water or other useful or treating fluid. In removing fluids, the fluid transfer unit 52 draws or creates a negative pressure to enable fluids, such as excess blood, to pass from the packing member through the holes 40 and along the delivery/draining tube 28 to the fluid transfer unit 52. As can be understood, the fluids drawn into the fluid transfer unit 52 can include both body fluids and previously delivered fluids from the fluid transfer unit 52. In the preferred embodiment, the fluid transfer unit 52 is a syringe or syringe-like member having a chamber 56 for containing a fluid to be delivered to the packing member 24 or for containing draining fluids from the packing member 24. At one end of the chamber 56 is a luer member 62 to which the end 64 of the delivery/draining tube 28 is connected. The chamber 56 slidably, but sealingly, receives a plunger 68, which is useful in forcing an irrigating fluid from the chamber 56 to the packing member 24 along the length of the delivery/draining tube 28. Alternatively, pulling on the syringe plunger in an opposite direction is useful in drawing draining fluid in a direction from the packing member 24 to the chamber 56. In another embodiment, the fluid transfer unit 52 includes a medicine container or bulb, which is able to hold a substantial dosage or amount of a medicine or other healing-type fluid.

Figure 4:
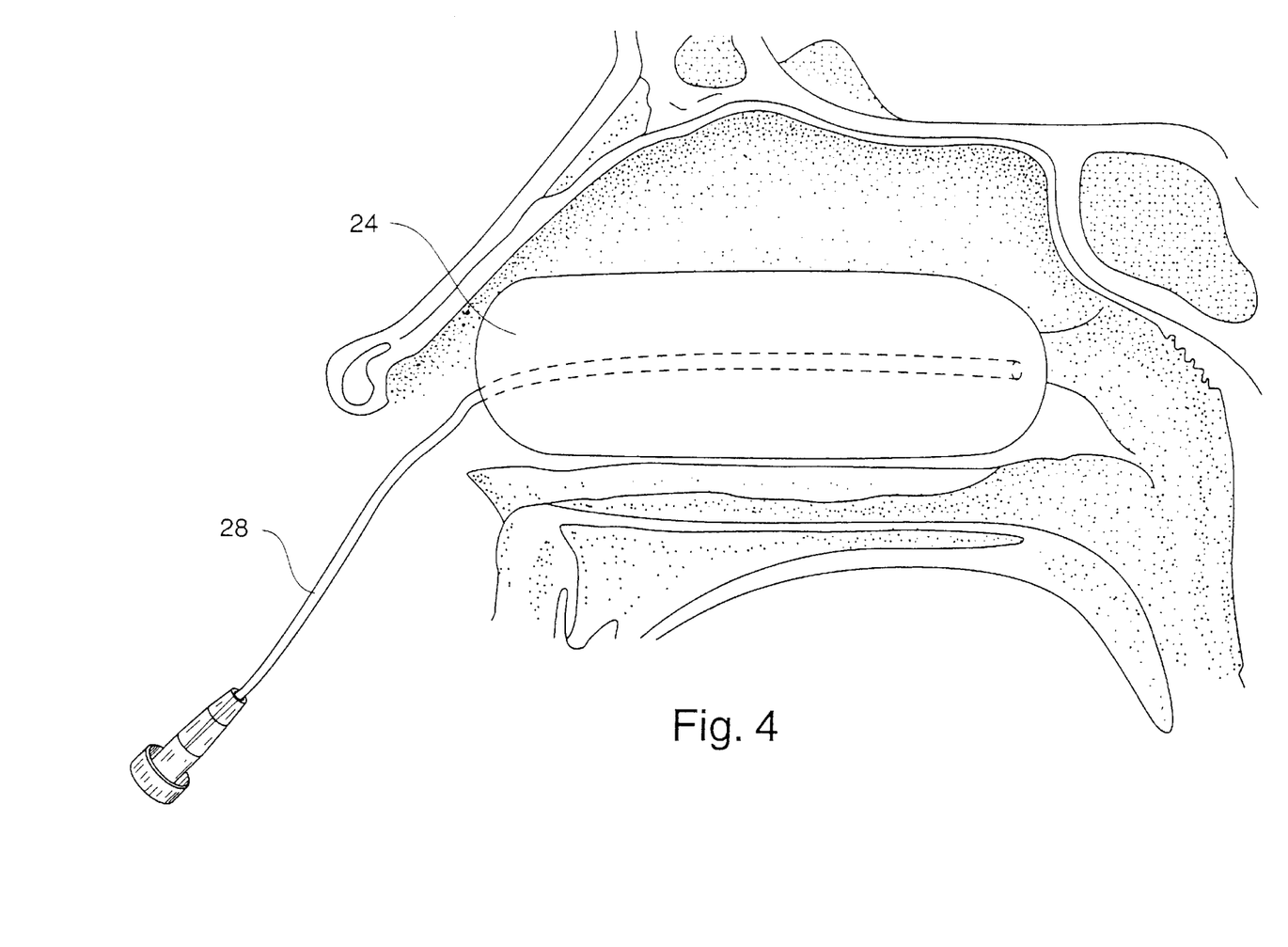
FIG. 4 illustrates the medical device in use in a nasal passage and the expanded state of the packing member for applying pressure to body cavity walls.

In using the medical device 20, reference is made to FIG. 4, which illustrates the packing member 24 in an expanded state in a body cavity and applying pressure to at least one wall of the body cavity. This particular body cavity is a nasal passage where it is desirable to control hemostasis. In this condition, the packing member 24 has received body fluid, such as blood, and absorbs the same. Upon absorption, the packing member 24 changes from its compressed state to its expanded state. At a desired expanded state, the packing member 24 applies the desired pressure to the one or more body walls in the body cavity. In many occurrences, the absorbed body fluid may not be sufficient to expand the packing member 24 to its desired size in order to apply the desired or necessary pressure. Accordingly, the user or practitioner causes desired fluid to be delivered from the fluid transfer unit 52 to the channel section 32 and into the packing member 24 through the one or more holes 40. Such additional fluid enables the packing member 24 to expand to its desired or necessary size. In many such circumstances, the volume of the delivered fluid for achieving the desired expansion is greater than the volume of the body fluid absorbed by the packing member 24. Preferably, the amount of pressure applied to at least one body wall of the body cavity is at least 2.3 psi and no greater than about 4.8 psi. In connection with the practitioner providing the desired fluid to achieve the proper expansion, often times the practitioner will observe or inspect the amount of expansion due to body fluid and make a determination that further fluid is necessary from the fluid transfer unit 52 in order to achieve this expansion. Once the packing member 24 is applying the desired pressure, it is in contact with the body wall and any body fluids that may still continue to exit from the body wall are immediately absorbed by the packing member 24 without traversing any space between the packing member 24 and the body wall. Additionally, when the packing member 24 has expanded and is properly performing its packing function, especially in the application of the present invention as a nasal pack, the tube length is sufficient to position portions thereof about the ear of the patient for positioning thereof in order to hold the delivery/draining tube 28 adjacent to the patient's head.

With the packing member 24 performing its pressure application function, it is often necessary or desirable to provide a fluid, e.g., an antibiotic, an anesthetic, a decongestant or an irrigating fluid, that contributes to the treating or healing process associated with the body cavity in which the packing member 24 is disposed. In such a case, the fluid is supplied by the fluid transfer unit 52 through the delivery/draining tube 28 to the packing member 24. From the packing member 24, this treating fluid is received by the cavity as it passes or seeps from the packing member 24. Furthermore, in using the medical device 20, it is not necessary to frequently remove the packing member 24 in order to replace the same, for example, because the packing member is saturated with fluids and must be removed to replace it with a drier packing member for further absorption purposes. Rather, the fluid transfer unit 52 is used, in combination with the channel section 32 and other portions of the delivery/draining tube 28, to remove fluids so that the packing member 24 can continue to absorb more fluids.

Important to the present invention, particularly the operation thereof, is the ability to remove the packing member 24 from the body cavity while substantially reducing or even eliminating discomfort or trauma to the patient. In prior art devices, it is typically the case that removal of the pack, such as a nasal pack, results in unwanted aggravation to the body tissue as the pack is removed from contacting the body cavity walls, as well as discomfort or a traumatizing experience as the pack engages different body parts as it is removed from the cavity. The method of the present invention involves supplying a rehydrating fluid, such as a friction reducing fluid or other type fluid, that provides a lining between the body cavity wall and the packing member 24 for reducing friction between the packing member 24 and the wall. This fluid is supplied essentially immediately before the packing member is removed from the body cavity. That is, in order to soften or make the packing member 24 more pliable, the packing member receives rehydrating fluid from the fluid transfer unit 52. Upon becoming sufficiently more flexible or pliable, the packing member 24 can be more readily manipulated to be removed without discomfort from the body cavity. Such removal after delivery of the rehydrating fluid for such a purpose is accomplished within at least about ten minutes, preferably within at least about five minutes, after the supplying of such irrigating fluid to the packing member. Relatedly, when supplying the rehydrating fluid for this purpose, the volume of such fluid that is absorbed by the packing member 24 is less than that absorbed by the packing member 24 when it was initially expanded for purposes of applying the necessary or desired pressure to the body cavity wall or walls.

Figure 5:
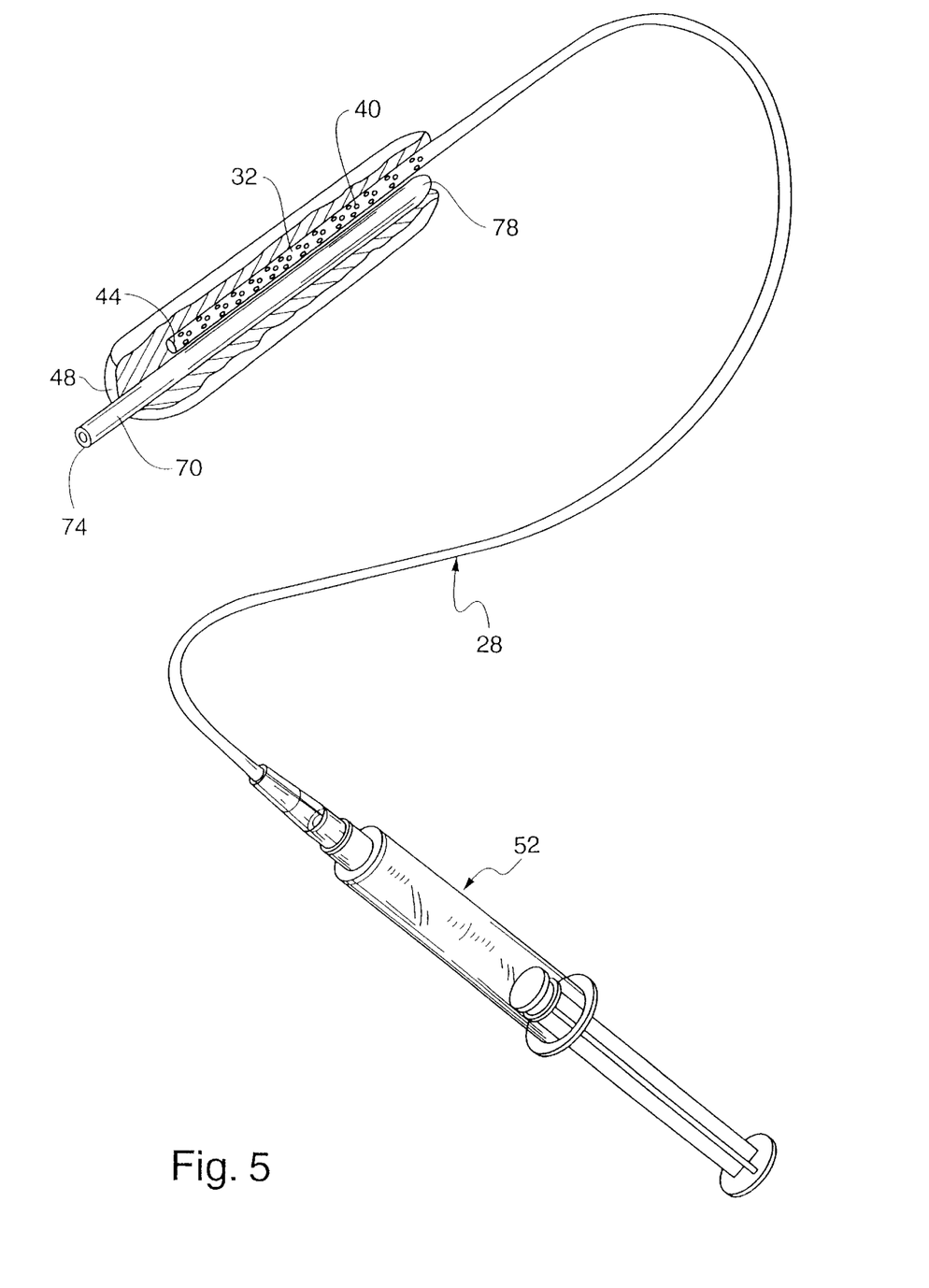
FIG. 5 illustrates another embodiment of the present invention in which the packing member receives a venting tube, in addition to the delivery/draining tube.
Figure 6:
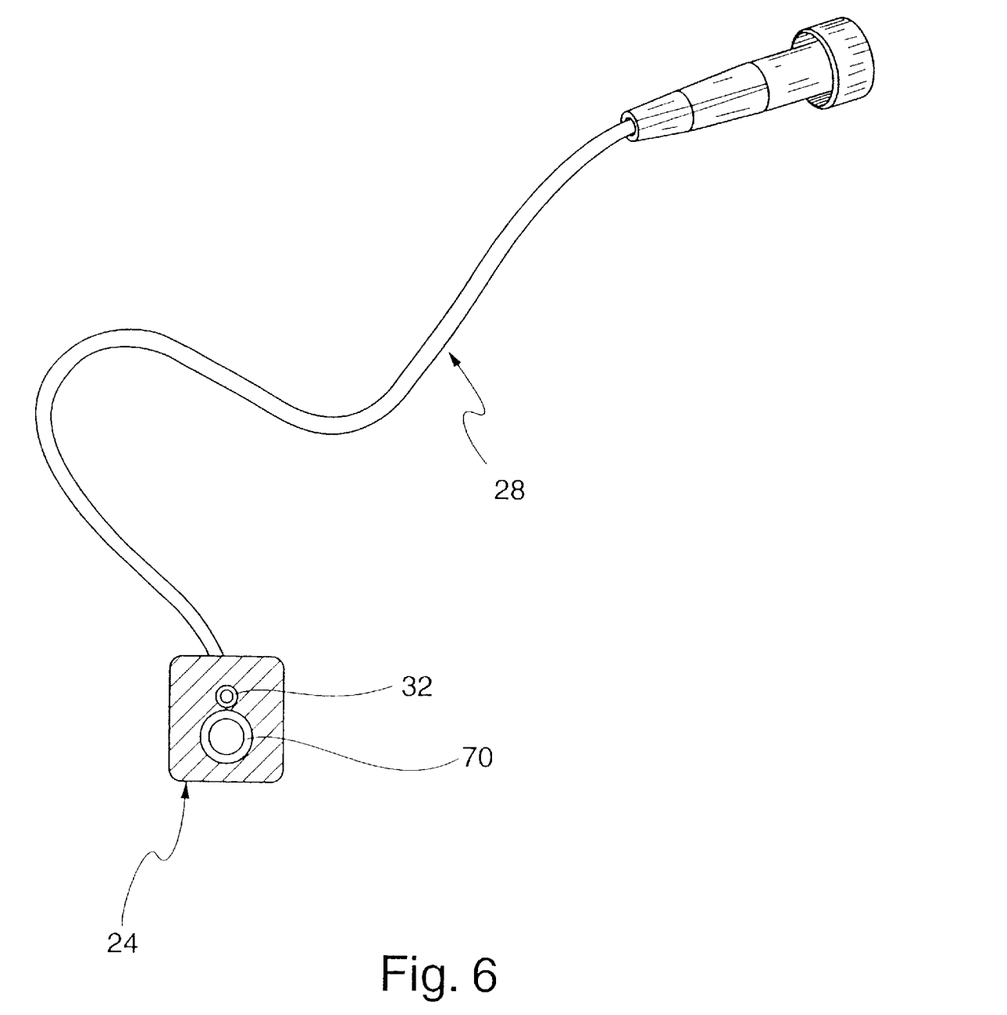
FIG. 6 illustrates a lateral cross-section of the packing member showing both the venting tube and the delivery/draining tube.
Figure 7:
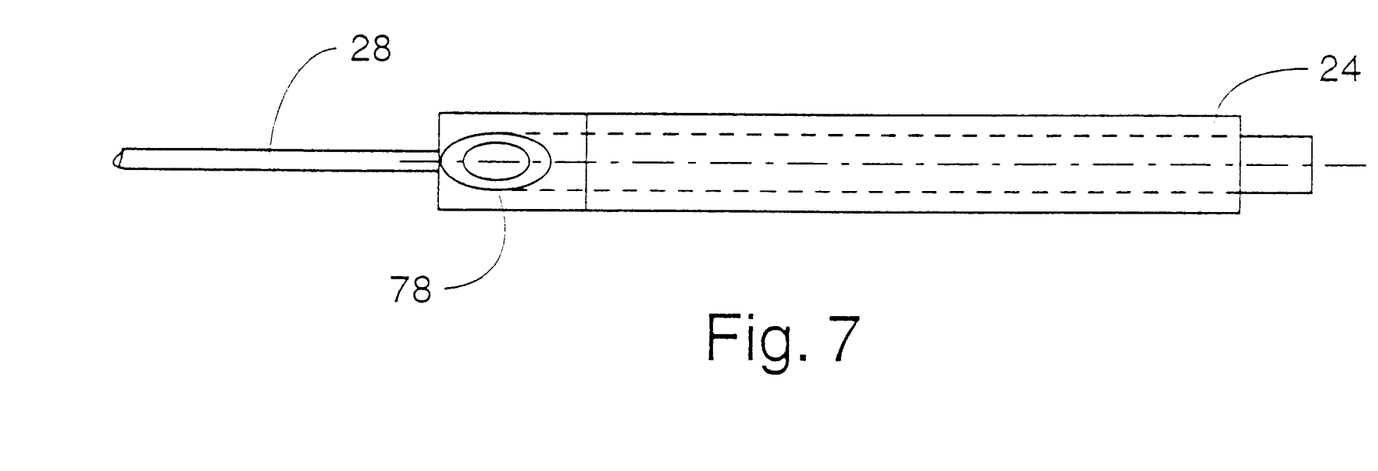
FIG. 7 is a bottom view of the packing member of FIG. 6 that illustrates the angled termination of the venting tube at its proximal end.

With reference to FIG. 5, another embodiment of the medical device 20 is illustrated. This embodiment is the same as that of FIG. 1 except that a venting tube 70 is provided within the body of the packing member 24. In such an embodiment, the channel 36 has a greater diameter or size to accommodate the width or diameter of the venting tube 70. The venting tube 70 is useful in permitting the patient to continue to breathe when the medical device 20 is used in a nasal body cavity. Consequently, by means of the venting tube 70, the patient is still able to breathe through his or her nose. The venting tube 70 includes a distal end 74 that extends from beyond the distal end 48 of the packing member 24. The proximal end 78 of the venting tube 70 does terminate at or near the opposite end of the packing member 24. As seen in FIG. 6, the venting tube 70 has a diameter that is typically greater than the diameter of the delivery/draining tube channel section 32. FIG. 7 illustrates a bottom view of the preferred embodiment that includes the venting tube 70, in which the proximal end 78 thereof is formed or cut at an angle. Consistent with this shape, the proximal end of the packing member 24 is also formed or cut at an angle that corresponds with the angle of the proximal end 78 of the venting tube 70. This configuration better permits the patient to breathe through his or her nose, while avoiding a potential blocking of this end of the venting tube 70 by portions of the body cavity walls.

Figure 8:
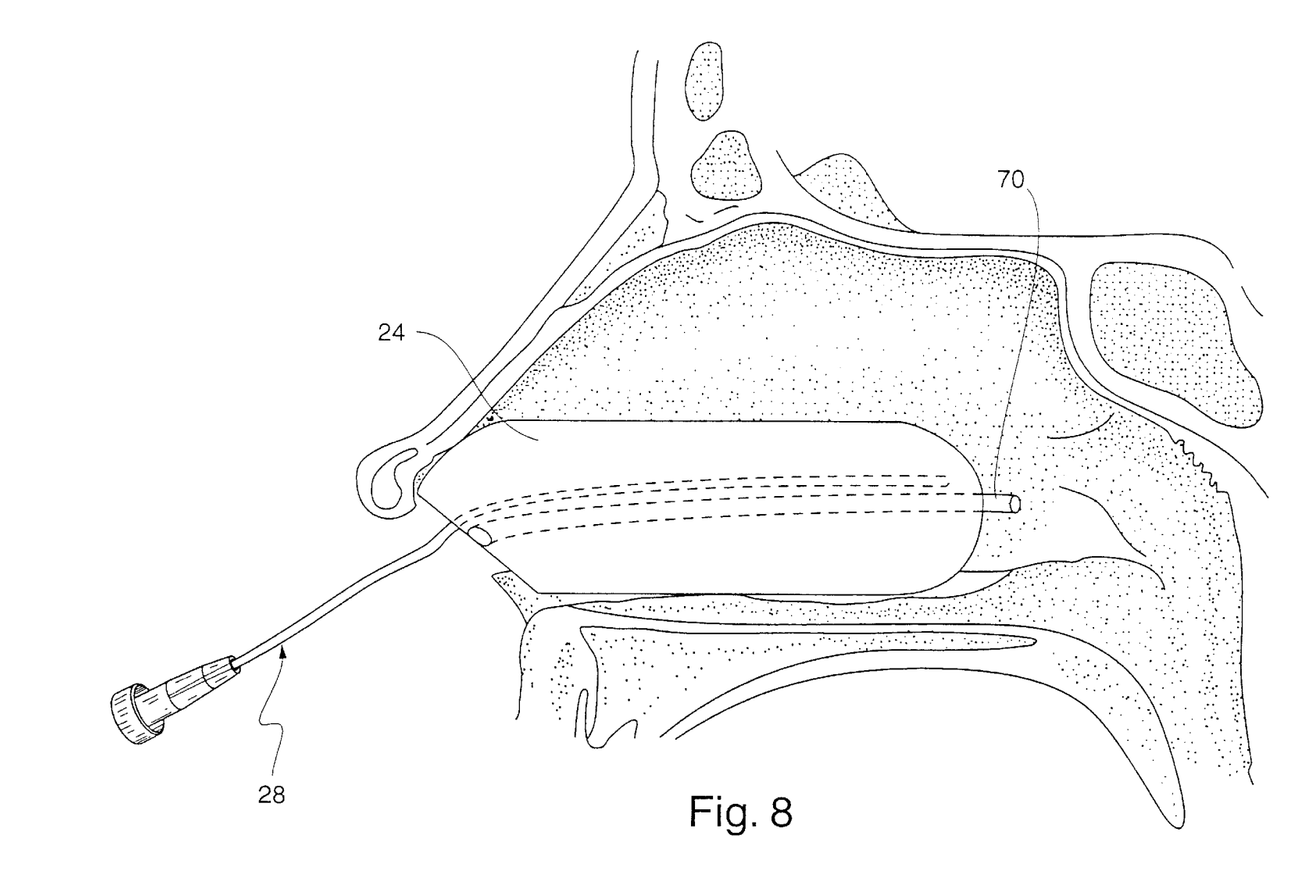
FIG. 8 illustrates the medical device that includes a venting tube positioned in a nasal passage for use in absorbing blood, applying pressure and providing delivery fluid.
Figure 9:
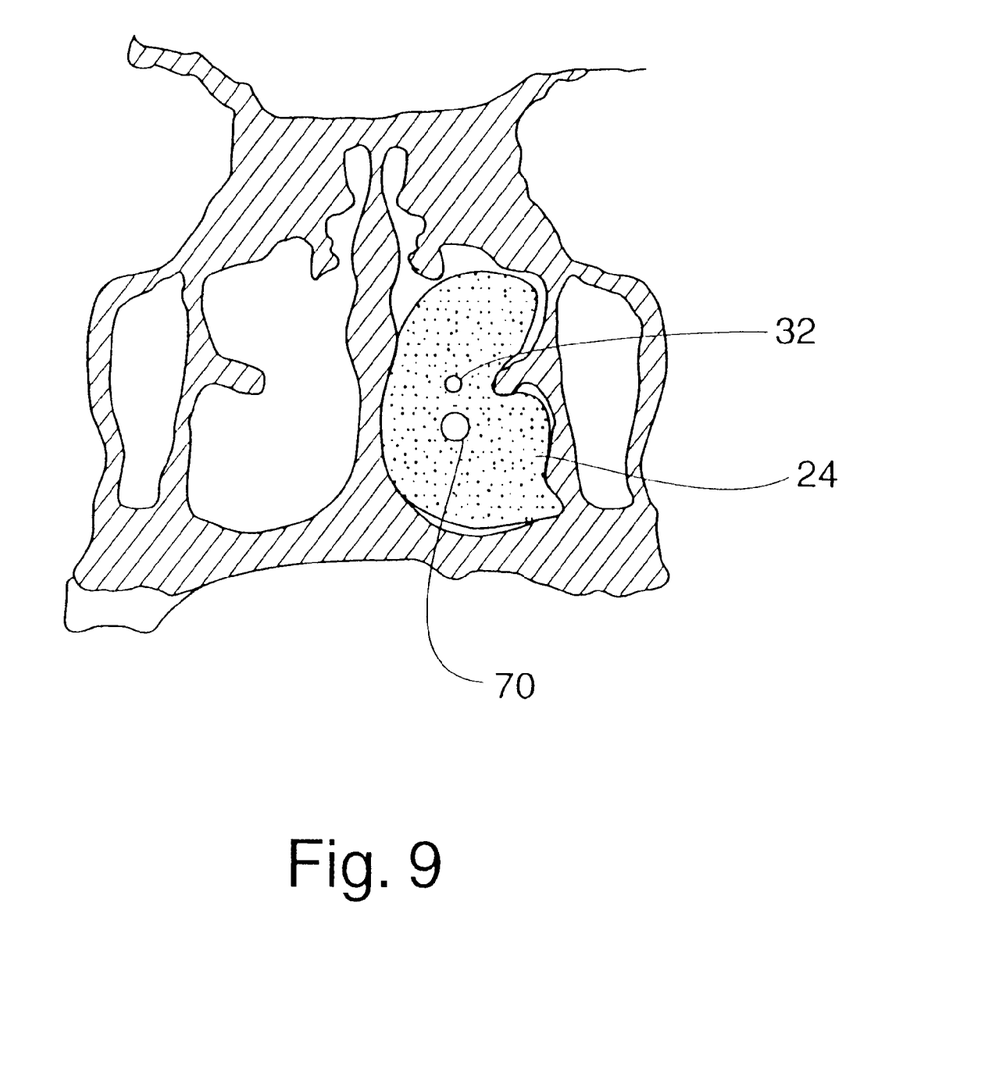
FIG. 9 illustrates the packing member of FIG. 8 in an expanded state in the nasal passage.

FIGS. 8 and 9 illustrate a use of this particular medical device 20 in a nasal passage. The insertion, use and removal of the medical device 20 of this embodiment is the same, except for the functions or features associated with the venting tube 70. That is, the packing member 24 is able to contact one or more walls in the body cavity and apply pressure, while the packing member is useful in absorbing fluid to assist in the removal or delivery of fluids relative to the body cavity.

Figure 10:
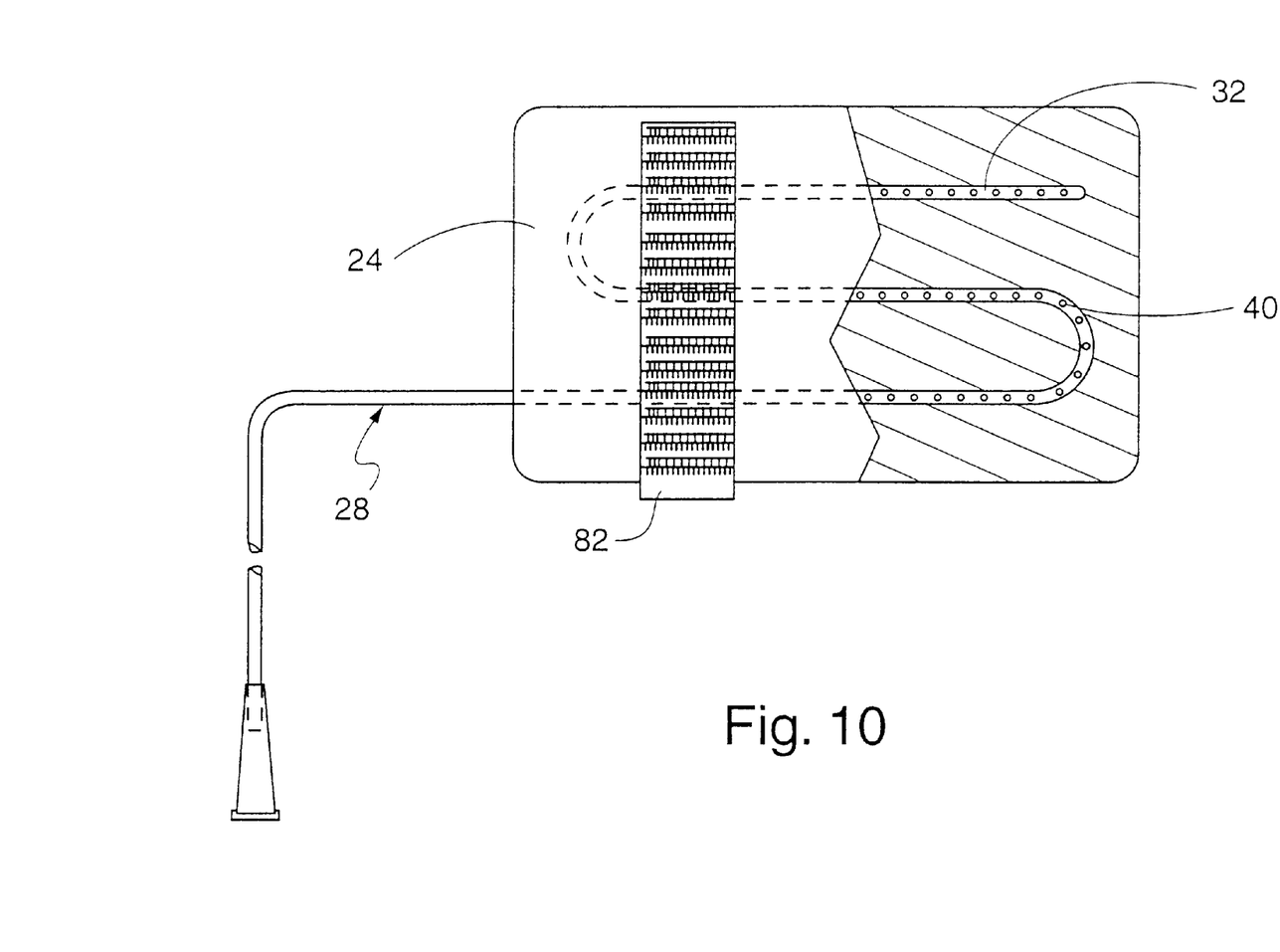
FIG. 10 illustrates another embodiment of the medical device in which the packing member is wider and in which the delivery/draining tube traverses the length of the packing member more than one time.

As previously noted, the present invention has utility or applications in a variety of body cavities of differing sizes. Another embodiment is useful in connection with wounds or other breaches in the body and where the medical device 20 is located outside of such a cavity or wound. With reference to FIG. 10, the packing member 24 is relatively wide to permit the delivery/draining tube 28 to substantially traverse the length of the packing member 24 more than one time. As before, the packing member 24, together with the delivery/draining tube 28 having the channel section 32, is able to deliver and remove fluids. In this embodiment, the packing member 24 is placed over a wound that is intended to receive an irrigating fluid, or alternatively, from which fluids are to be drained, such as blood. A strap 82 or other connector is joined to the packing member 24. The strap 82 is useful in affixing the packing member 24 to a body part, such as an arm having a wound therein. In a related application, this device is located within a breech in the body where it is able to absorb blood or other body fluid for withdrawal thereof. Additionally or alternatively, a desired fluid can be supplied to the breech using the packing member 24.

Figure 11:
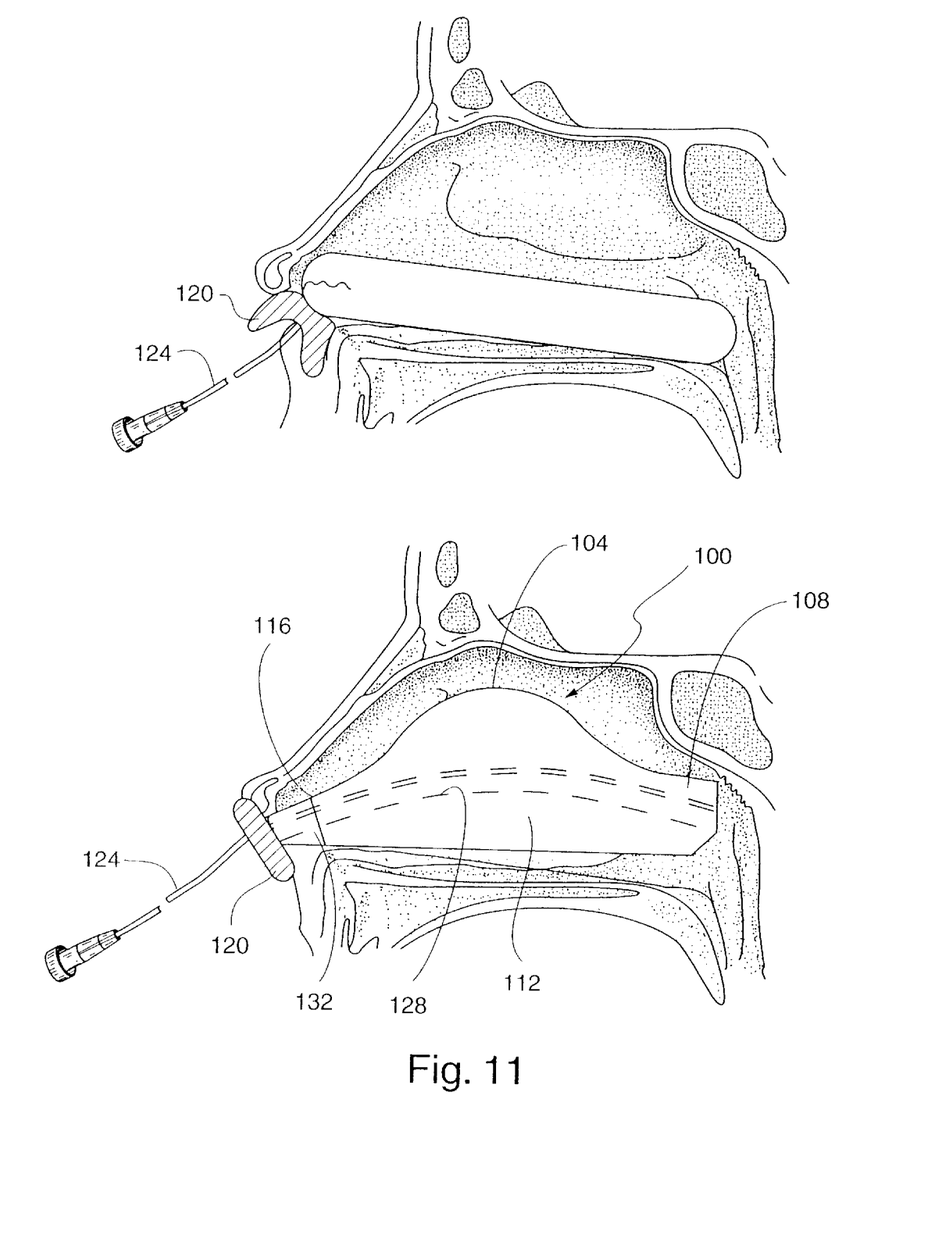
FIG. 11 illustrates yet another embodiment of the medical device having a particular geometric configuration, together with a wrap member disposed about an anterior section thereof.

In another embodiment, a medical device 100 is configured in a desired geometric shape for insertion in a nasal cavity for applying pressure and absorbing fluid. With reference to FIG. 11, the medical device 100 includes a packing member 104 for positioning in a nasal cavity that is intended to optimize the pressure applying and absorbing functions. The packing member is definable as having three sections integrally formed together, namely: a posterior section 108, a body or mid section 112 and an anterior section 116. The body section 112 is intermediate the posterior and anterior sections 108, 116. Preferably, the medical device 100 includes an anchor member 120 joined to the anterior section 116. The anchor member 120 is used to prevent movement of the packing member 104 in a direction inwardly relative to the nasal cavity to avoid aspiration of the packing member 104 further into the patient, which further insertion might jeopardize the patient's well-being. Like the other embodiments, the medical device 100 can include a delivery/draining tube 124 that is located along the length of the length of the packing member 104 and has holes for outputting or receiving liquid. An air channel 128 is also formed throughout the length of the packing member 104 to provide an appropriate breathing passage for the patient. The medical device 100 is further characterized by the inclusion of a wrap member 132 that is disposed about at least portions of the anterior section 116. The portions of the anterior section 116 that are covered are typically those portions of the packing member 104 that have relatively greater exposure to air. Consequently, in the absence of the wrap member 132, such portions would unwantedly contact and/or adhere to the walls of the cavity or other parts of the nose. In such a case, increased difficulty in removing the medical device 100 from the cavity might be encountered due to such an adhesion that would be caused by such portions being open to the air or ambient environment. To overcome this potential unwanted adhesion, the wrap member 132 is made of a material different from that of the packing member 104. Such material is preferably impermeable, such as a plastic- or rubber-like material. With the wrap member 132 in place, there is no adherence between the outer surface of the wrap member 132 and any part of the nasal cavity or nose in order to facilitate removal of the medical device 100 when desired.

Figure 12:
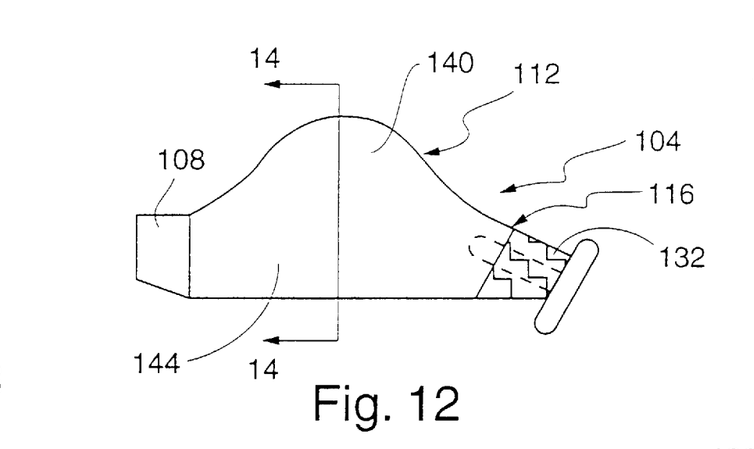
FIG. 12 is a side elevational view of the medical device of FIG. 11, which includes the packing member, anchor member and wrap member disposed about an anterior section of the packing member.
Figure 13:
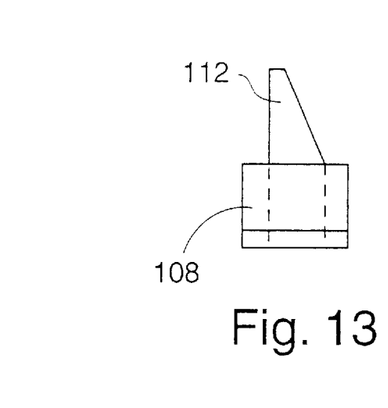
FIG. 13 is a rear view of the embodiment of the medical device of FIG. 11.

With reference to FIGS. 12–15, further aspects of the medical device 100 are described in greater detail, particularly the geometry and geometric constraints associated with the packing member 104. As seen in FIG. 12, a boundary is definable between the body section 112 and the posterior section 108 of the packing member 104. This boundary is due to a clear and immediate difference in a width dimension between the body section 112 and the posterior section 108. As seen in FIG. 13, the width of the posterior section 108 is substantially greater than the width of the body section 112 at this boundary or juncture. The greater width of the posterior section 108 provides a desired lateral extent of these portions of the packing member 104 in the nasal cavity to better contribute to the applying of pressure at this area and maintaining of the packing member 104 in place. It is further essential, with respect to the posterior section 108, that its dimensions be maintained in a key range of dimensions. Specifically, the width of the posterior section 108 must be in the range of about 1.0–3.0 cm; the height thereof must be in the range of about 1.0–3.0 cm; and the depth thereof must be in the range of about 0.5–3.0 cm.

Figure 14:
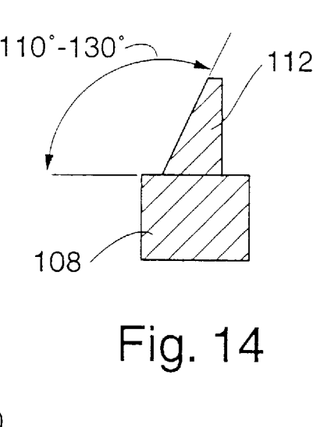
FIG. 14 illustrates the lateral section of the packing member taken through lines 14—14 of FIG. 12.

As illustrated in FIG. 12, the mid or body section 112 has substantially greater length and volume (occupies more space) than each of the other two sections 108, 116. The body section 112 is definable as having an upper curved section 140 and a lower base section 144. The curved section 140 is formed by a gradual increasing of the height from the base section 144 inwardly relative to the anterior section 116 and the posterior section 108. As seen in FIG. 14, the width of the body section 112 gradually decreases from the boundary or top of the base section 144 to the tip or apex of the curved section 140. An angle is defined due to the decreasing width. This angle defined between the top of the base section 144 and the surface of the curved section 140 is different from 90 degrees. Such an angle is formed on one of the two sides of the body section 112 depending upon whether the medical device 100 is to be inserted in the left or right nostril of the patient. This particular angle is confined to a range of angles of 110°–130°. In addition to limitations on the range of angles, the volume of the body section 112 is confined to the range of about 22 $cm^3$–50 $cm^3$. With this volume, the body section 112 applies most of the pressure and supplies or absorbs most of the liquid relative to the nasal cavity.

As also seen in FIG. 12, the anterior section 116 is definable at a boundary or juncture between the body section 112 and the anterior section 116. The anterior section 116 is relatively closer to the nasal cavity opening and, as previously noted, is relatively more exposable to the air. The wrap member 132 covers or surrounds most, if not all, of the anterior section portions. The wrap member 132 is disposed about such portions in a way that prevents them from noticeably expanding, unlike the body and posterior sections 112, 108. That is, the wrap member 132 is sufficiently tightly wrapped about such anterior section portions to prevent any such expansion. The wrap member 132 also has key dimensions, particularly it is desirable to maintain the length of the wrap member 132 along the length of the anterior section 116 as short as possible, with the range of lengths being from about 0.5–2 cm. Likewise, the range of the diameter of the wrap member 132 about the anterior section 116 must be in the range of about 0.5–3 cm.

Figure 15:
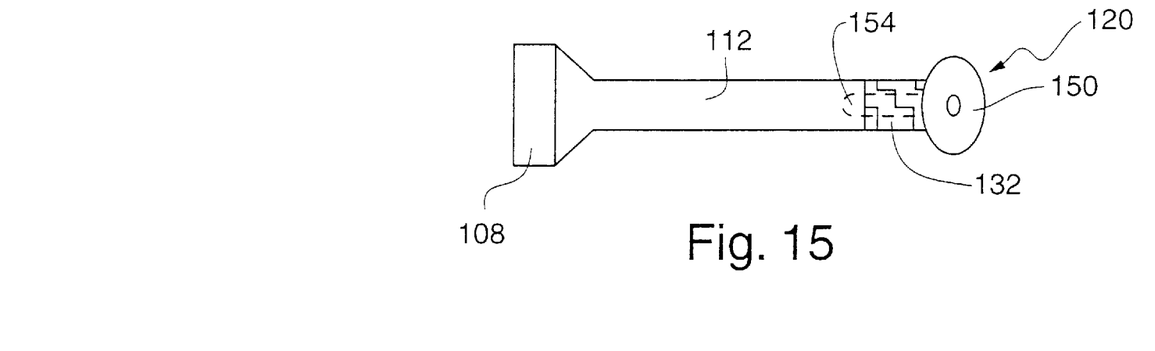
FIG. 15 illustrates a bottom view of the medical device of FIG. 11.

Referring to FIG. 15, as well as FIG. 12, the anchor member 120 has a flange 150 that extends outwardly from the anterior section 116. A shaft 154 is joined to the flange 150 and is fixedly positioned within the anterior section 116. In one embodiment, a channel or elongated opening is formed through about the middle of the anterior section 116 and is of a size to provide a tight or friction fit between the anterior section 116 and the shaft 154. The flange 150 has a substantially greater diameter than that of the shaft 154 and is of a sufficient size to prevent it from entering the nasal cavity under normal or proper usage.

In making and/or assembling the medical device 100, the packing member 104 can be formed from a sheet of absorbent material, like the other embodiments discussed herein, using cutting, stamping, molding and/or other similar processes that achieve the afore-noted geometric shape. In providing the wrap member 132 about the portions of the anterior section 116, in one embodiment, the wrap member 132 includes shrink wrap material that is positioned about such portions. After being positioned at the desirable location about such portions, the shrink wrap material is subjected to suitable heat causing the wrap member 132 to shrink about and tightly join to the anterior section portions wherein the wrap member 132 cannot be pulled or slid off the end of the anterior section 108.

With regard to use of the medical device 100, it is similar to embodiments previously described herein. The device 100 is inserted into the nasal cavity in a relatively compressed state. The posterior section 108 has a width to extend across the nasal cavity and provide a holding or anchoring function at the rear of the nasal cavity, particularly applying desired pressure when it absorbs fluid. The body section 112 occupies a substantial majority of the nasal cavity space and expands to provide the desired pressure application when it absorbs liquid, either delivered to it or received from the cavity. The anterior section 116 with wrap member 132 is positioned adjacent to the nasal cavity opening. When the portions of the packing member 104 absorb fluid, the anterior section portions having the wrap member 132 disposed thereabout do not expand or, at most, expand nominally or minimally. The wrap member 132 prevents any adhesion or attachment that might occur between this portion of the medical device and parts of the nose. The flange 150 of the anchor member 120 is located outwardly of the nasal cavity and has a diameter of a size that inhibits it being inserted under normal operation into the nasal cavity. The anchor member 120 holds the packing member 104 in place in the nasal cavity and substantially contributes to preventing the packing member 104 from further movement inwardly relative to the nasal cavity.

The foregoing discussion of the invention has been presented for purposes of illustration and description. Further, the description is not intended to limit the invention to the form disclosed herein. Consequently, variations and modifications commensurate with the above teachings, within the scope or knowledge of the relevant art, are within the scope of the present invention. The embodiments discussed hereinabove are further intended to explain the best known mode of practicing the invention and to enable others skilled in the art to utilize the invention in such, or in other embodiments, and with the various modifications required by their particular application or uses of the invention. It is intended that the appended claims be construed to include alternative embodiments to the extent permitted by the prior art.

What is claimed is:

1. A method for absorbing fluid while applying pressure, comprising:

inserting a packing member having a length, a thickness and a first size into an existing nasal cavity having an open beginning and an end and in which, before said inserting, said existing nasal cavity open beginning is used to receive said packing member, wherein said packing member having an outer surface that absorbs fluid in said nasal cavity and said outer surface being in open communication with and in proximity to said nasal cavity open beginning during said inserting;

receiving fluid through at least one hole formed in a tube having a channel section positioned within said thickness of said packing member, said receiving step including obtaining supplied fluid from outside of said nasal cavity, said obtaining step includes delivering said supplied fluid as one of an antibiotic, an anesthetic, a decongestant and an irrigating fluid;

absorbing fluid by said packing member with said packing member expanding to a second size due to said absorbed fluid and in which parts of said packing member are spaced from said nasal cavity when said packing member has said first size while said packing member parts contact portions of said nasal cavity when said packing member has said second size; and applying pressure to said nasal cavity portions when said packing member expands to said second size and in which said pressure is absent when said packing member has said first size.

2. A method, as claimed in claim 1, further including:

attaching said tube to a patient's head.

3. A method, as claimed in claim 1, further including:

providing a venting tube within said packing member to permit breathing therethrough.

4. A method, as claimed in claim 1, further including:

forming a proximal end of said packing member at an angle, different from 90°, and providing a venting tube having an angle at one of its ends substantially the same as said angle of said proximal end of said packing member.

5. A method, as claimed in claim 1, wherein:

said packing member has an anterior end and a posterior end and in which said inserting step includes positioning said anterior end immediately adjacent said open beginning.

6. A method, as claimed in claim 5, wherein:

said anterior end is located less than one-quarter of said length of said packing member from said open beginning.

7. A method, as claimed in claim 1, wherein:

said receiving step includes supplying fluid from outside of said nasal cavity to said packing member by moving a plunger inwardly relative to a syringe barrel.

8. A method, as claimed in claim 1, further including:

connecting a syringe using a luer member thereof to said tube.

9. A method for absorbing fluid while applying pressure, comprising:

inserting a packing member having a length, a thickness and a first size into an existing nasal cavity having an open beginning and an end and in which, before said inserting, said existing nasal cavity open beginning is used to receive said packing member, wherein said packing member having an outer surface that absorbs fluid in said nasal cavity and said outer surface being in open communication with and in proximity to said nasal cavity open beginning during said inserting;

receiving fluid through at least one hole formed in a tube having a channel section positioned within said thickness of said packing member, said receiving step including obtaining supplied fluid from outside of said nasal cavity, said obtaining step includes delivering said supplied fluid as a rehydrating fluid immediately before said packing member is removed from said nasal cavity;

absorbing fluid by said packing member with said packing member expanding to a second size due to said absorbed fluid and in which parts of said packing member are spaced from said nasal cavity when said packing member has said first size while said packing member parts contact portions of said nasal cavity when said packing member has said second size; and applying pressure to said nasal cavity portions when said packing member expands to said second size and in which said pressure is absent when said packing member has said first size.

10. A method for absorbing fluid while applying pressure, comprising:

inserting a packing member having a length, an anterior end, a posterior end, a thickness and a first size into an existing nasal cavity having an open beginning and an end and in which, before said inserting, said existing nasal cavity open beginning is used to receive said packing member, wherein said packing member has an outer surface that absorbs fluid in said nasal cavity, with said outer surface being in open communication with and in proximity to said nasal cavity open beginning during said inserting, said inserting step including positioning said anterior end immediately adjacent said open beginning wherein said anterior end is located no greater than about one-quarter of said length of said packing member from said open beginning after completion of said positioning step;

connecting a syringe, having a barrel, a luer member at an end of said barrel and a plunger, using said luer member to a tube having a plurality of holes in communication with said packing member;

receiving fluid through said plurality of holes, said receiving step including supplying fluid from outside of said nasal cavity to said packing member by moving said plunger inwardly relative to said syringe barrel;

absorbing fluid by said packing member with said packing member expanding to a second size due to said absorbed fluid and in which parts of said packing member are spaced from said nasal cavity when said packing member has said first size while said packing member parts contact portions of said nasal cavity when said packing member has said second size; and     applying pressure to said nasal cavity portions when said packing member expands to said second size and in which said pressure is absent when said packing member has said first size.

11. A method, as claimed in claim 10, wherein:

said inserting step includes using a flange, which is connected to said anterior end of said packing member, having a sufficient size to prevent said flange from entering said nasal cavity.

12. A method, as claimed in claim 10, further including:

providing a venting tube within said packing member to permit breathing therethrough.

13. A method, as claimed in claim 10, further including:

forming a proximal end of said packing member at an angle, different from 90°, and providing a venting tube having an angle at one of its ends substantially the same as said angle of said proximal end of said packing member.

* * * * *